(12) United States Patent
Schläpfer et al.

(10) Patent No.: US 7,666,207 B2
(45) Date of Patent: Feb. 23, 2010

(54) FIXATION DEVICE FOR BONES

(75) Inventors: Fridolin Schläpfer, Glarus (CH); Martin Hess, Holstein (CH); Konrad Tagwerker, Basel (CH)

(73) Assignee: Synthes USA, LLC, West Chester, PA (US)

( * ) Notice: Subject to any disclaimer, the term of this patent is extended or adjusted under 35 U.S.C. 154(b) by 27 days.

(21) Appl. No.: 11/485,833

(22) Filed: Jul. 13, 2006

(65) Prior Publication Data

US 2006/0271053 A1 Nov. 30, 2006

Related U.S. Application Data

(63) Continuation of application No. 10/456,535, filed on Jun. 9, 2003, now abandoned, which is a continuation of application No. PCT/CH00/00654, filed on Dec. 8, 2000.

(51) Int. Cl.
*A61B 17/70* (2006.01)

(52) U.S. Cl. ...................................... 606/246

(58) Field of Classification Search ............... 606/61, 606/72, 73, 60, 105, 65, 66, 67, 246, 264–267, 606/270–275, 279, 286, 287, 297, 300, 301, 606/304–306, 308–312, 314–319, 321
See application file for complete search history.

(56) References Cited

U.S. PATENT DOCUMENTS

| | | | |
|---|---|---|---|
| 3,025,853 A | 3/1962 | Mason | |
| 4,103,683 A | 8/1978 | Neufeld | |
| 4,710,075 A * | 12/1987 | Davison | 408/202 |
| 4,978,349 A | 12/1990 | Frigg | |
| 5,300,074 A | 4/1994 | Frigg | |
| 5,501,684 A | 3/1996 | Schlapfer et al. | |
| 5,688,273 A | 11/1997 | Errico et al. | |
| 5,741,256 A | 4/1998 | Bresina | |
| 5,888,221 A | 3/1999 | Gelbard | |
| 6,187,007 B1 | 2/2001 | Frigg et al. | |

FOREIGN PATENT DOCUMENTS

DE 29600879 3/1996

(Continued)

OTHER PUBLICATIONS

International Search Report, dated Aug. 31, 2001, from International Application No. PCT/CH00/00654.

(Continued)

*Primary Examiner*—Eduardo C Robert
*Assistant Examiner*—David Comstock
(74) *Attorney, Agent, or Firm*—Stroock & Stroock & Lavan LLP

(57) ABSTRACT

A device for fixation of vertebral bodies including a longitudinal support with a central axis and two or more anchoring elements. Each anchoring element having a longitudinal axis, a front end, and a back end. The longitudinal axis of each anchoring element may be arranged at an angle of between 65 degrees and 115 degrees relative to the central axis of the longitudinal support, while the anchoring elements are designed to abut the back end. The anchoring elements may be shaped in the form of a blade toward the front end.

11 Claims, 10 Drawing Sheets

FOREIGN PATENT DOCUMENTS

| | | |
|---|---|---|
| EP | 0599847 B1 | 4/1997 |
| JP | 08-257034 | 10/1996 |
| JP | 11-178838 | 7/1999 |
| WO | WO91/01691 | 2/1991 |
| WO | WO 98/05263 | 2/1998 |
| WO | WO 98/31293 | 7/1998 |
| WO | WO 98/52482 | 11/1998 |
| WO | WO 00/10473 | 3/2000 |

OTHER PUBLICATIONS

First Japanese Office Action, issued for Japanese Patent Application No. 2002-547394.

* cited by examiner

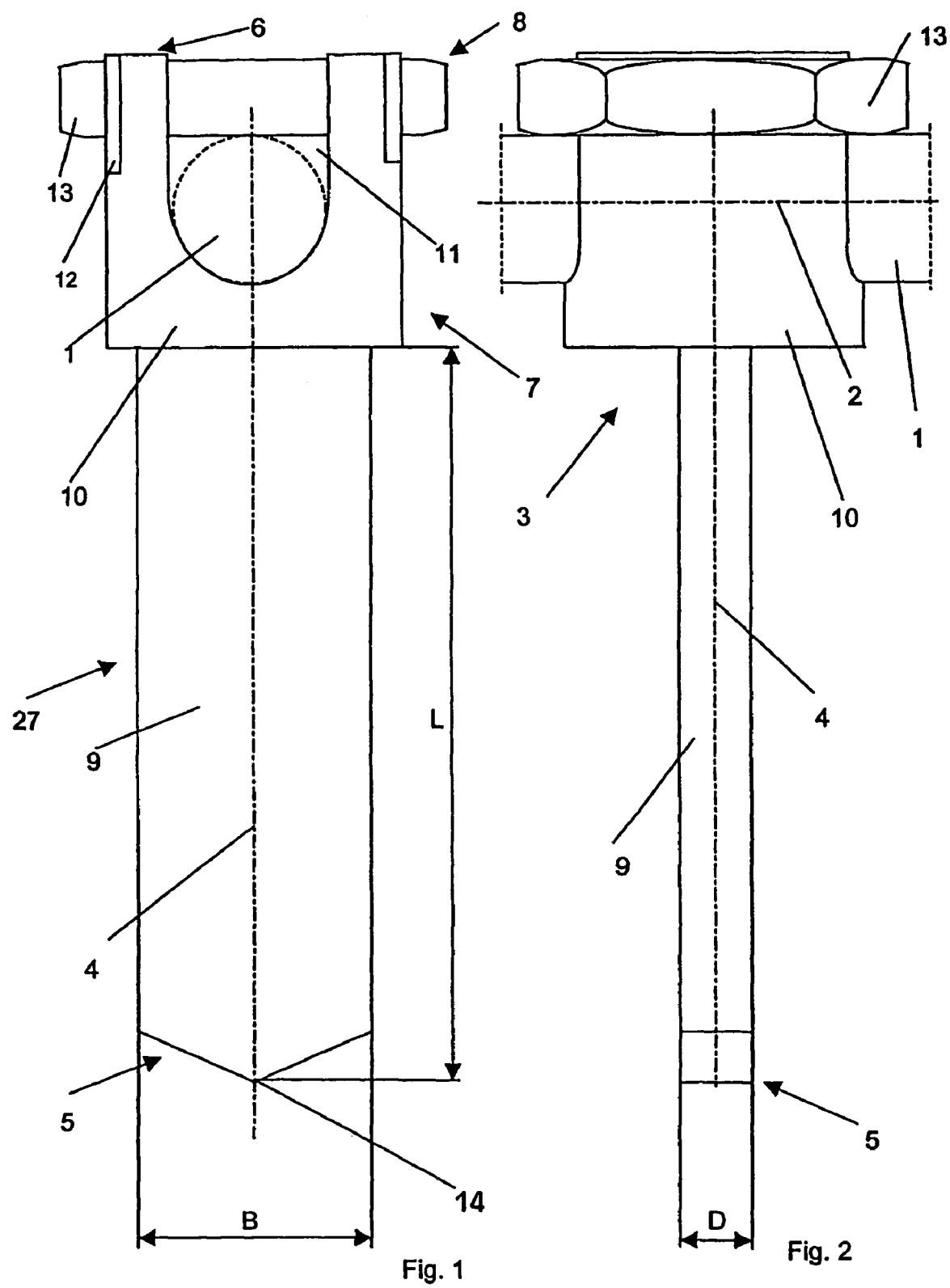

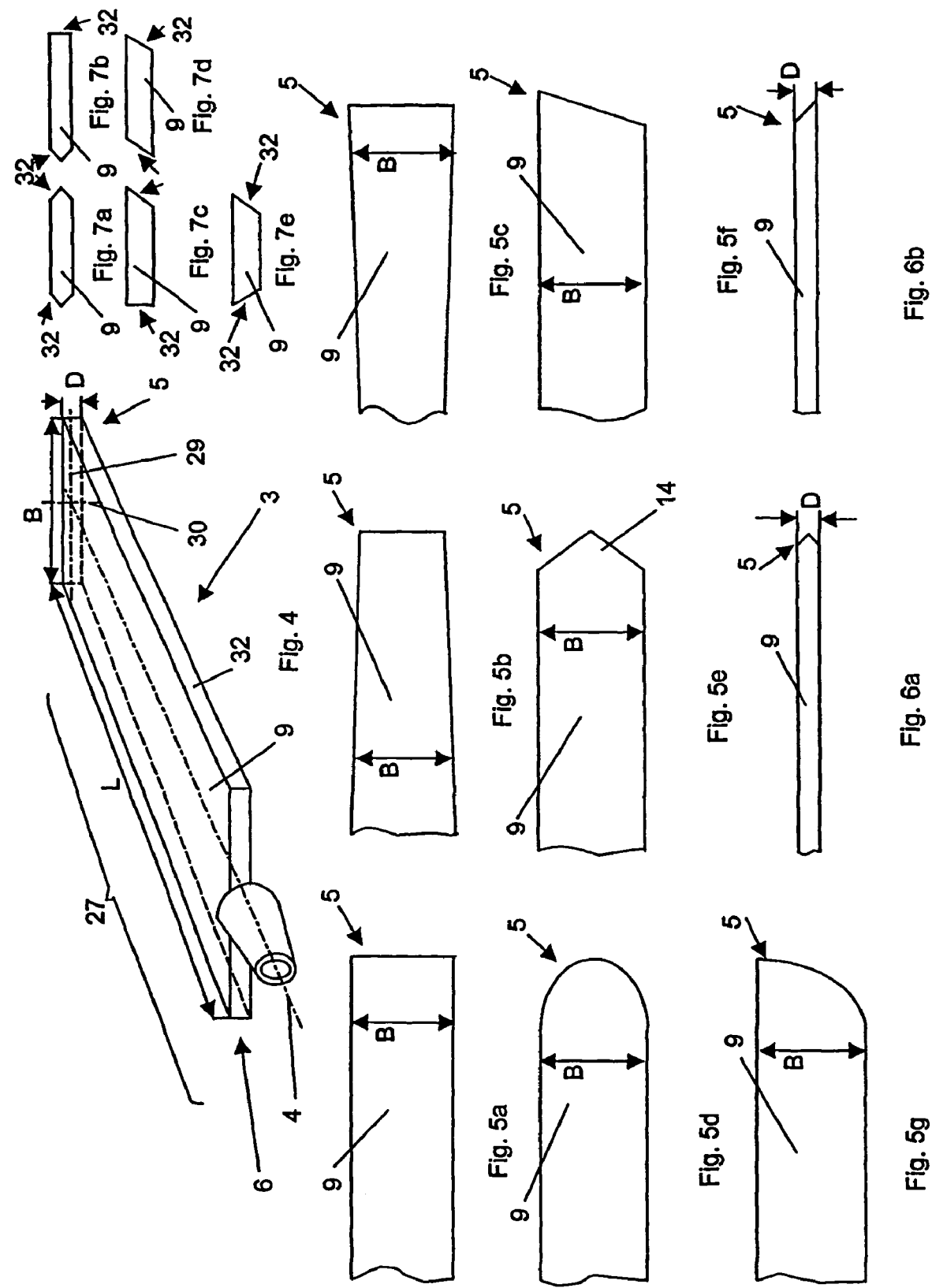

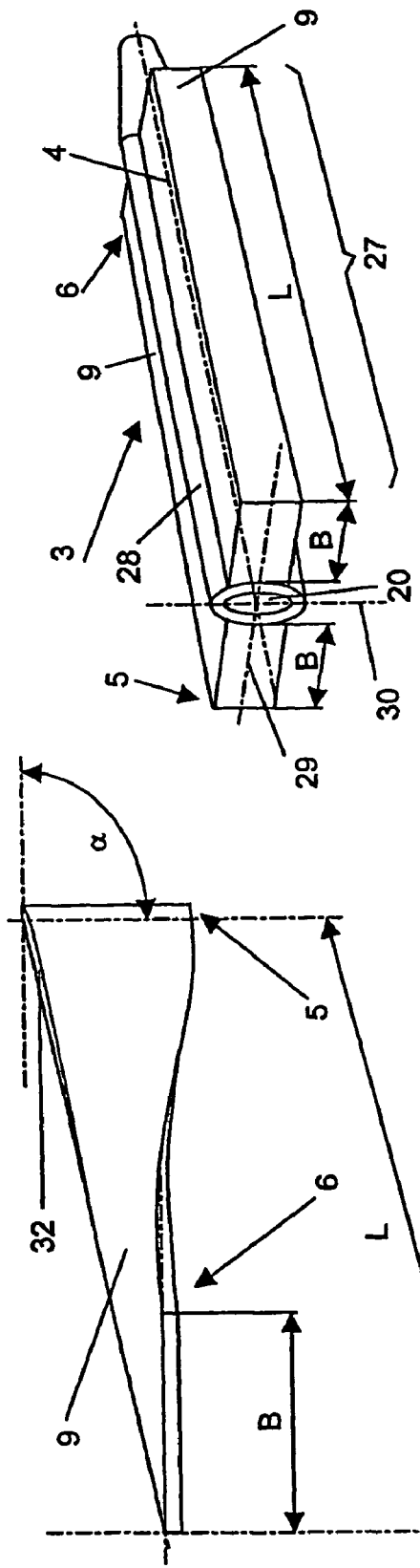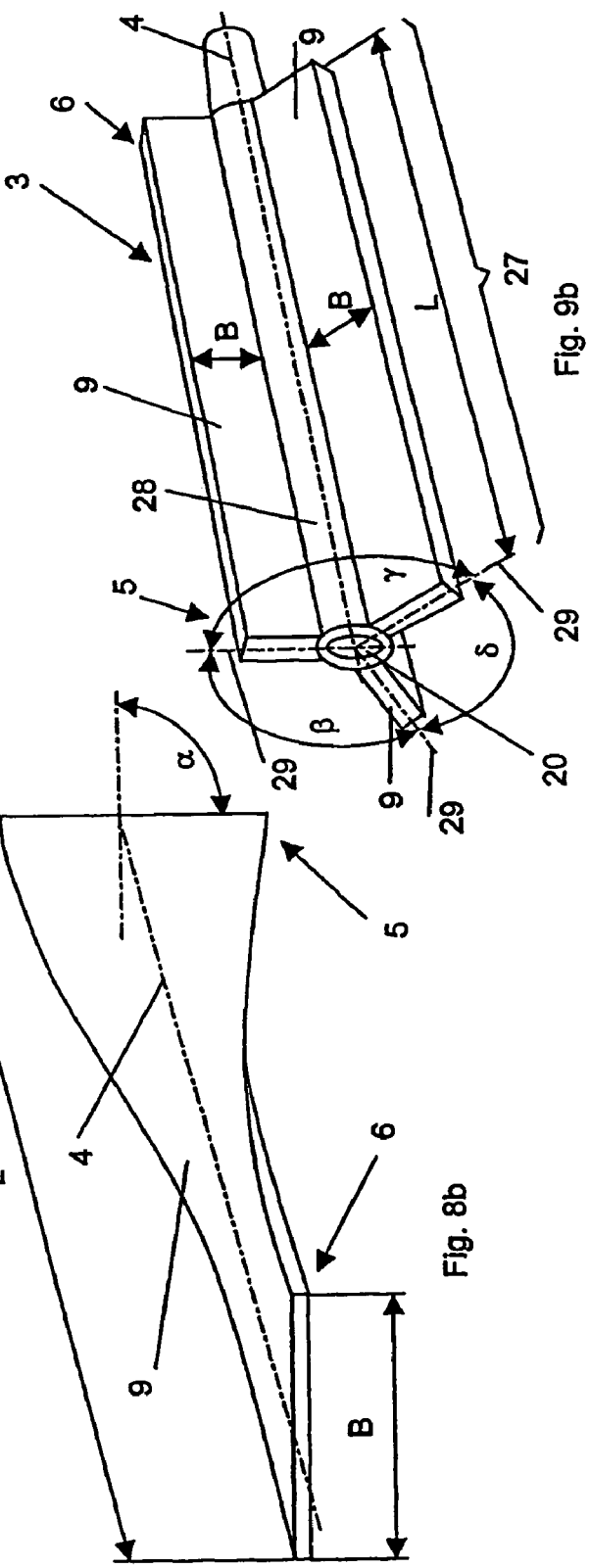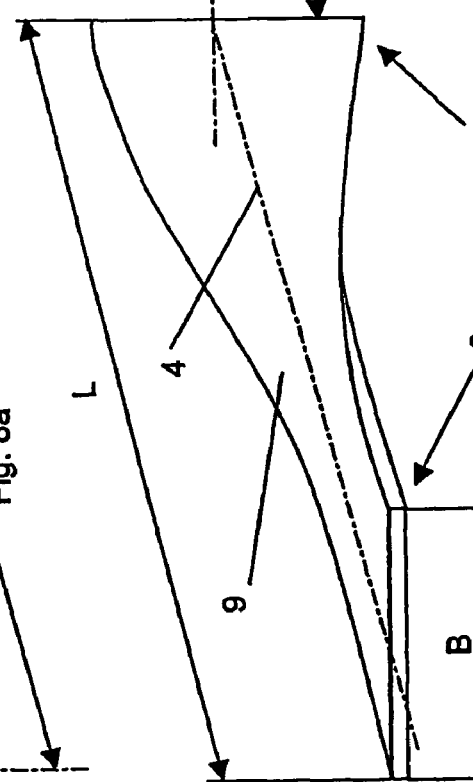

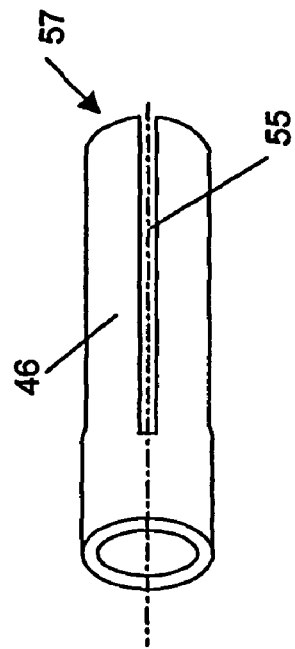
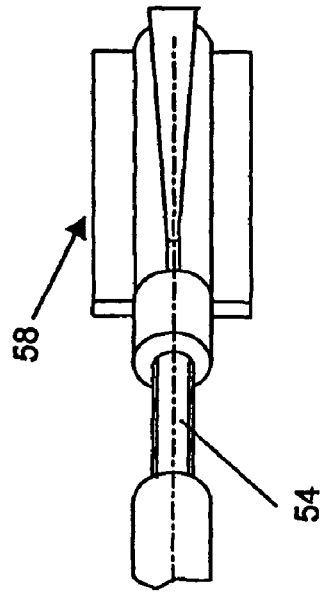
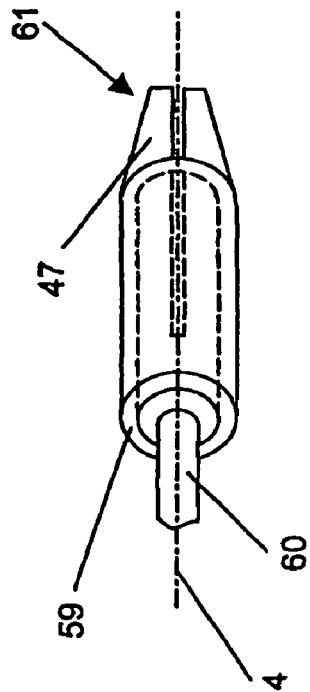
Fig. 16b
Fig. 17b
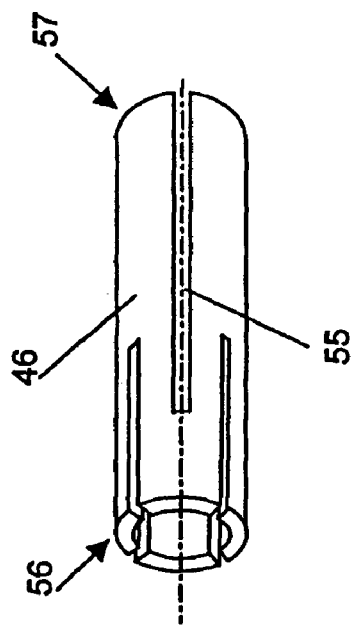
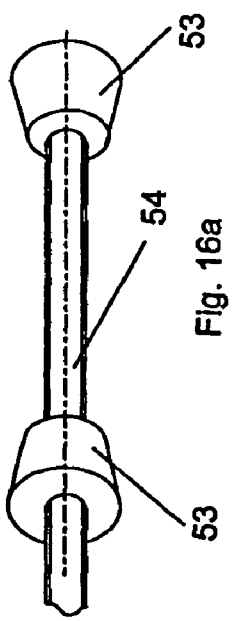
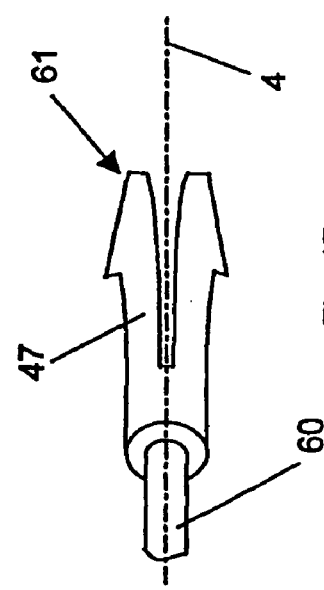
Fig. 16a
Fig. 17a

FIXATION DEVICE FOR BONES

CROSS-REFERENCE TO RELATED APPLICATIONS

This is a continuation of U.S. patent application Ser. No. 10/456,535 filed Jun. 9, 2003 now abandoned, entitled "Device for Fixing Bones in Relation to One Another," which is expressly incorporated herein by reference in its entirety, which is a continuation of the U.S. national stage designation of copending International Patent Application PCT/CH00/00654, filed Dec. 8, 2000, the entire content of which is expressly incorporated herein by reference thereto.

FIELD OF THE INVENTION

The present invention relates generally to orthopaedic fasteners, and in particular to a device for fixation of vertebral bodies.

BACKGROUND OF THE INVENTION

Instabilities in spinal-column motion segments that may be caused by vertebral fractures, degenerative changes, etc. often require that the segments in question be fused. In order to ensure the immobilization of the segments to be fused as required for bone fusion, the corresponding segments are often stabilized with a fixation system. Fixation systems may either be inserted and anchored from the posterior, whereby the anchoring is done by means of bone screws in the pedicles, or from the anterior or antero-lateral, in which case the anchoring is done by means of bone screws in the vertebral bodies.

The quality with which fixation systems are anchored is heavily dependent on the quality of the bone structures. This is especially true of antero-laterally anchored fixation systems. The greater the degree of osteoporosis, the greater the danger that the bone screws will cut through the bone when subjected to even small loads. The use of thick screws reduces the risk of cutting through the bone. However, overly thick screws should be avoided lest there be excessive destruction of the bone structure in the vertebral body.

Known approaches in the related art for reducing the risk of the anchoring elements cutting through the bone are presented in DE 296 00 879 and in WO 00/10473. These publications deal basically with a hollow screw that is screwed into the vertebral body. The hollow screw does not need to displace a great deal of bone, because a peg of bone maybe left in place in the center of screw. However, when the hollow screw is being screwed in, the vascular supply to the peg of bone left in the center may be impaired, which may lead to complications, especially in osteoporotic bones. Also, in bones with still-functioning repair mechanisms, the hollow screw may be so heavily in-grown that it may be difficult to remove it if the area is to be inspected or, if removed, it will do serious damage to the bone (in some cases, for example, it has proved to be impossible to remove hollow screws inserted into the cervical vertebral column).

In connection with the surgical treatment of fractures in long bones, intramedullary stabilization techniques have been developed that, with modification, may also be successfully employed in the spinal column to solve the problem of anchoring anterior and antero-lateral spinal-column fixation systems. Intramedullary pins, for instance, may be used to splint fractured tubular bones by providing an intramedullary connection between the proximal portion of the broken tubular bone and its distal portion. Because of its geometry, however, the intramedullary pin can withstand only minor rotational and axial loads. This may not be potentially problematic as long as the fractured bone is able under axial load to maintain its height and the fracture is more or less diaphyseal. As soon as multi-fragment fractures arise, however, the intramedullary pin typically has to be anchored proximally and distally. In this way, the intramedullary pin can provide not only splinting but, as in the case of the spinal column, may act as a proximately and distally anchored longitudinal support that can transfer forces and moments at all levels from proximal to distal. In the case of the intramedullary pin, the anchoring implants may be screws that are run transversely through the bone and the intramedullary pin on the proximal and distal sides. In patients with osteoporosis and in cases where the fractures lie close to the joint, anchoring the intramedullary pin with screws is often not a satisfactory approach. Also, spiral-twisted blade-shaped implants known in the related art and as used in clinical practice are not particularly suitable for use on spinal column.

SUMMARY OF THE INVENTION

The present invention relates to the fixation of bones, and in particular to the fixation of vertebral bodies. In one embodiment, the present invention is comprises a longitudinal support with a central axis and n anchoring elements ($2 \leq i \leq n$). Each anchoring element having a longitudinal axes, a front end, and a back end. The longitudinal axis of each anchoring elements may be arranged at an angle of between 65° and 115° relative to the central axis of the longitudinal support, while the anchoring elements are designed to abut the back end. The anchoring elements may be shaped in the form of a blade toward the front end. The angle-variable connection of the anchoring elements may be achieved by virtue of the fact that at the back end each anchoring element comprises means for receiving the longitudinal support with attachment means that can be controlled from the back end for reversibly locking the connection between the longitudinal support and the anchoring element. The locked connection may prevent relative movement between the longitudinal support and the anchoring element and takes up forces and moments in all three axial directions of a three-dimensional coordinate system.

BRIEF DESCRIPTION OF THE DRAWINGS

Preferred features of the present invention are disclosed in the accompanying drawings, wherein similar reference characters denote similar elements throughout the several views, and wherein:

FIG. 1 is a top view of an embodiment of the device according to the invention;

FIG. 2 is a side view of the embodiment of the device according to the invention shown in FIG. 1;

FIG. 4 is a perspective view of an embodiment of the anchoring element;

FIGS. 5a to 5g are top views of various embodiments of the anchoring element;

FIGS. 6a and 6b are side views of various embodiments of the anchoring element;

FIGS. 7a to 7e are cross-sections of anchoring elements of various embodiments of the anchoring element;

FIGS. 8a and 8b are perspective views of twisted anchoring segments in various embodiments of the anchoring element;

FIGS. 9a and 9b are perspective views of anchoring segments consisting of multiple blades in various embodiments of the anchoring element;

FIGS. 16a and 16b are perspective views of devices for anchoring a transport device for inserting the anchoring element;

FIGS. 17a and 17b are perspective views of another device for anchoring a transport device for inserting the anchoring element;

DETAILED DESCRIPTION OF THE PREFERRED EMBODIMENTS

Figure 3:
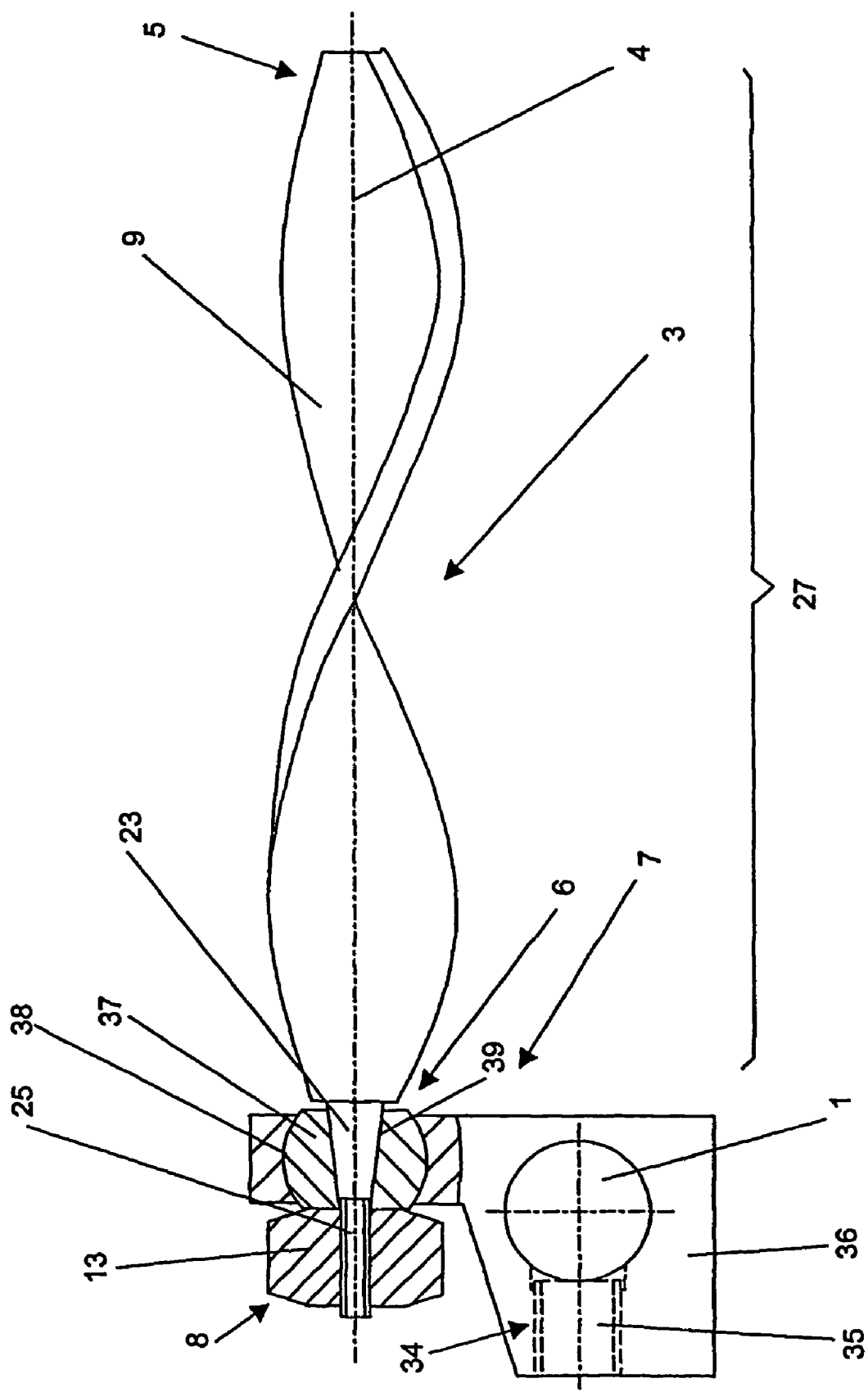
FIG. 3 is a side view of another embodiment of the device according to the invention.

FIGS. 1 and 2 show an embodiment of the device according to the invention that comprises an anchoring element 3 with receiving means 7 for a longitudinal support 1 at the back end 6 of the anchoring element 3. The receiving means 7 consists of a receiving head 10 that is essentially circular-cylindrical and is coaxial with a longitudinal axis 4 of the anchoring element 3, with a channel 11 that is open toward the back end 6 to receive the longitudinal support 1. In this case, the longitudinal support 1 is received in such a way that its central axis 2 runs vertical to the longitudinal axis 4. In an area between the front end 5 and the receiving head 10, the anchoring element 3 contains an anchoring segment 27, which is designed as an essentially parallelepiped blade 9. Viewed vertically with respect to the longitudinal axis 4, the blade 9 has a rectangular cross-section with a width B and a thickness D. At the front end 5 of the anchoring element 3, the width B of the blade 9 converges to a point 14. Moreover, external threading 12 that is concentric to the longitudinal axis 4 on the receiving head 10 and a nut 13 that can be screwed onto this external threading 12 are arranged at the back end 6 of the anchoring element 3 as immobilizing means 8 so that when the nut 13 is tightened, the longitudinal support 1 is axially clamped in the channel 11, thereby locking the anchoring element 3 to the longitudinal support 1.

The embodiment shown in FIG. 3 of the device according to the invention encompasses an anchoring element 3, which has as an anchoring segment 27 a spiral-shaped blade 9 that is coaxial to the longitudinal axis 4. At the back end 8 of the anchoring element 3, coaxial to the longitudinal axis 4, are located a cone segment 23 that abuts the anchoring segment 27 and, also attached coaxially thereto, a threaded pin 25. The receiving means 7 consists essentially of a connecting element 36 with a hole in it, wherein the longitudinal support 1 is mounted so as to be able to move coaxially with respect to the central axis 2 (FIG. 2) and can be secured in place with a stop screw 35. Running next to the longitudinal support 1 in connecting element 36 is a cavity 38 in the shape of a hollow sphere that runs through the connecting element 36, in which a slotted tensioning element 37 in the shape of a two-base spherical segment is mounted. The tensioning element 37 is equipped with an inner cone 39, in which the cone segment 23 can be received in the anchoring element 3. Because the anchoring element 3 and the connecting element 36 are connected by means of the tensioning element 37 that can be rotated in the cavity around three axes that are vertical to one another, the angle between the central axis 2 of the longitudinal support 1 and the longitudinal axis 4 of the anchoring element 3 can be varied. With a nut 13 that can be screwed onto the threaded pin 25 at the end, the cone segment 23 is pulled into the inner cone 39 of the tensioning element 37, thus expanding said segment radially. In the cavity 38, clamping is done in such a way that the anchoring element 3 is locked in the connecting element 36. Such a connection between the longitudinal support 1 and a pedicle screw as an anchoring element 3 is described in EP 0 599 847. Instead of the cone segment 23 and the threaded pin 25, at the back end 6 of the anchoring element 3 there can be a ball head that can be connected to the longitudinal support 1 by means of a device to connect a longitudinal support 1 to an anchoring element 3 that is designed as a pedicle screw, as disclosed in WO 98/52482.

FIG. 4 shows an embodiment of the anchoring segment 27 that abuts the back end 6 of the anchoring element 3.j over a length L. The anchoring segment 27 consists essentially of a flat blade 9 that has a length L, a width B, and a thickness D. Length L and thickness D enclose the lateral surfaces 32 of the blade. When viewed vertically with respect to the longitudinal axis 4, the cross-section of the blade 9 encompasses a first transverse axis 29, which runs in the plane of the lateral surfaces 32 and is vertical with respect to the longitudinal axis 4, and a second transverse axis 30, which is vertical with respect to the lateral surfaces 32 and with respect to the longitudinal axis 4. The ratio of width B to thickness D is basically between 1 and 14 and preferably between 3 and 6. Owing to this ratio of width B to thickness D, the implant can be inserted into a vertebral body without major destruction of the bone. The blade 9 is then aligned in the bone with allowance for the action of load. If the blade 9 is implanted in a vertebral body in such a way that the first transverse axis 29 runs parallel to the longitudinal axis of the spinal column, the blade 9 has great resistance to bending stress but is in an unfavorable position with respect to cutting through the bone. If, however, the blade 9 is implanted in the vertebral body in such a way that the second transverse axis 30 runs parallel to the longitudinal axis of the spinal column, the blade 9 is placed in a more favorable position as regards cutting through the bone, although this is achieved at the expense of reduced resistance to bending.

For example, the blade 9 can be designed as follows:

a) in the shape of a parallelepiped with a length L, a thickness D, and a width B (FIG. 5a);

b) in the shape of a wedge with a width B that converges toward the front end 5 (FIG. 5b);

c) in the shape of a wedge with a width B that diverges toward the front end 5 (FIG. 5c);

d) viewed from the top, the blade 9 is designed to be convex at the front end 5 (FIG. 5d);

e) viewed from the top, the blade 9 tapers to a point 14 with even or uneven sides (FIG. 5*e*);

f) viewed from the top, the blade 9 is beveled on one side at the front end 5 (FIG. 5*f*);

g) viewed from the top, the blade 9 is rounded on one side at the front end 5 (FIG. 5*g*);

h) in a longitudinal section running parallel to the lateral surfaces 32, the blade 9 tapers to a point at the front end 5 with even or uneven sides (FIG. 6*a*);

i) in a longitudinal section running parallel to the lateral surfaces 32, the blade 9 is beveled on one side at the front end 5 (FIG. 6*b*);

j) in a cross-section that is a vertical with respect to the longitudinal axis 4, both of the lateral edges of the blade 9 that lie in the lateral surfaces 32 taper into a point (FIG. 7*a*);

k) in a cross-section that is a vertical with respect to the longitudinal axis 4, a lateral edge of the blade 9 that lies in a lateral surface 32 tapers into a point (FIG. 7*b*);

l) in a cross-section that is a vertical with respect to the longitudinal axis 4, a lateral edge of the blade 9 that lies in a lateral surface 32 is beveled (FIG. 7*c*);

m) in a cross-section that is a vertical with respect to the longitudinal axis 4, both lateral edges of the blade 9 that lie in the lateral surfaces 32 are equally beveled (FIG. 7*d*); and n) in a cross-section that is a vertical with respect to the longitudinal axis 4, the two lateral edges of the blade 9 that lie in the vertical surfaces 32 are beveled in diametrically opposed ways (FIG. 7*e*).

FIGS. 8*a* and 8*b* show two embodiments of a twisted blade 9. FIG. 8*a* shows a blade 9 that is twisted by an angle of twist a over length L around an edge of the blade 9 that encloses length L and abuts one of the lateral surfaces 32. FIG. 8*b* show the blade 9 that is twisted by a angle of twist α over length L around the longitudinal axis 4 as well. The twisting can be left-handed or right-handed. For twisting length Lv and angle of twist α, the lead of the twist can be defined as follows:

$$\text{Lead } S = Lv° \, 360°/\alpha[']. $$

In cases where the blade 9 is designed in shape of this kind of spiral, a lead of between 60 mm and 300 mm and preferably between 100 mm and 240 mm is advantageous.

FIG. 9*a* shows another embodiment of the anchoring element 3 with a combination of blades 9. The anchoring element 3 comprises an anchoring segment 27 with two blades 9 that are connected by a hollow 28 that is arranged coaxially with regard to the longitudinal axis 4 over the entire length of the anchoring element 3. In this case the two blades 9 are arranged in such a way that their first transverse axes 29 lie in one plane. A hole 20 runs through the hollow 28 concentrically with respect to the longitudinal axis 4.

The embodiment of the anchoring element 3 that is shown in FIG. 9*b* is another combination of multiple blades 9 that comprises three blades 9 arranged in the shape of a star. The one lateral surfaces 32 (FIG. 4) of the three blades 9 are connected to a coaxial hollow cylinder 28 parallel to the longitudinal axis 4, whereby the first transverse axes 29 of the blades 9 enclose the central angles β, γ, δ. In the embodiment depicted here, the central angles β, γ, δ are equal, i.e., β=γ=δ, while in other embodiments the blades 9 can be arranged with different central angles as required by the given situation. An anchoring element 3 that comprises three or more blades 9 can also be designed in the shape of a spiral.

In the case of intramedullary-pin systems, the blade-shaped anchoring implant is hammered in. Hammering in or near the spinal column is not recommended since there is the danger that vital neurologic and vascular structures may be damaged.

Possible ways of inserting the anchoring element 3 in a controlled manner using a transport device 15 are depicted in FIGS. 10-13. The transport device 15 shown in FIG. 10 includes a transport screw 16 with a screw tip 17, a screw shaft 18, a threaded segment 21 adjacent to the screw tip 17, and a drive means 19, whereby the drive means 19 can be operated from the back end 6 of the anchoring element 3. The transport screw 16 is able to turn freely relative to the anchoring element 3. If the transport screw 16 is turned by means of the screwdriver 49, it screws through the bone and pulls the anchoring element 3 along with it.

Figure 10:
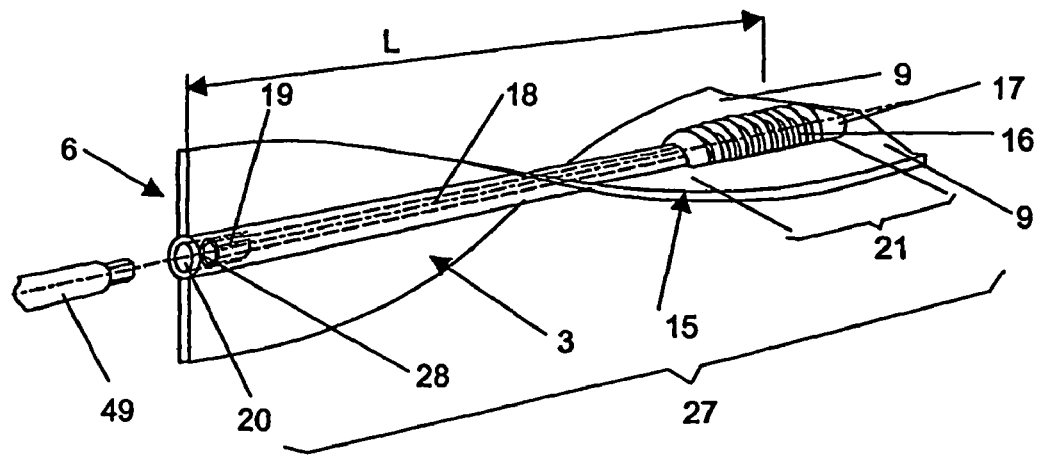
FIG. 10 is a perspective view of an embodiment of a spiral-shaped anchoring element that is equipped with a transport screw.
Figure 11:
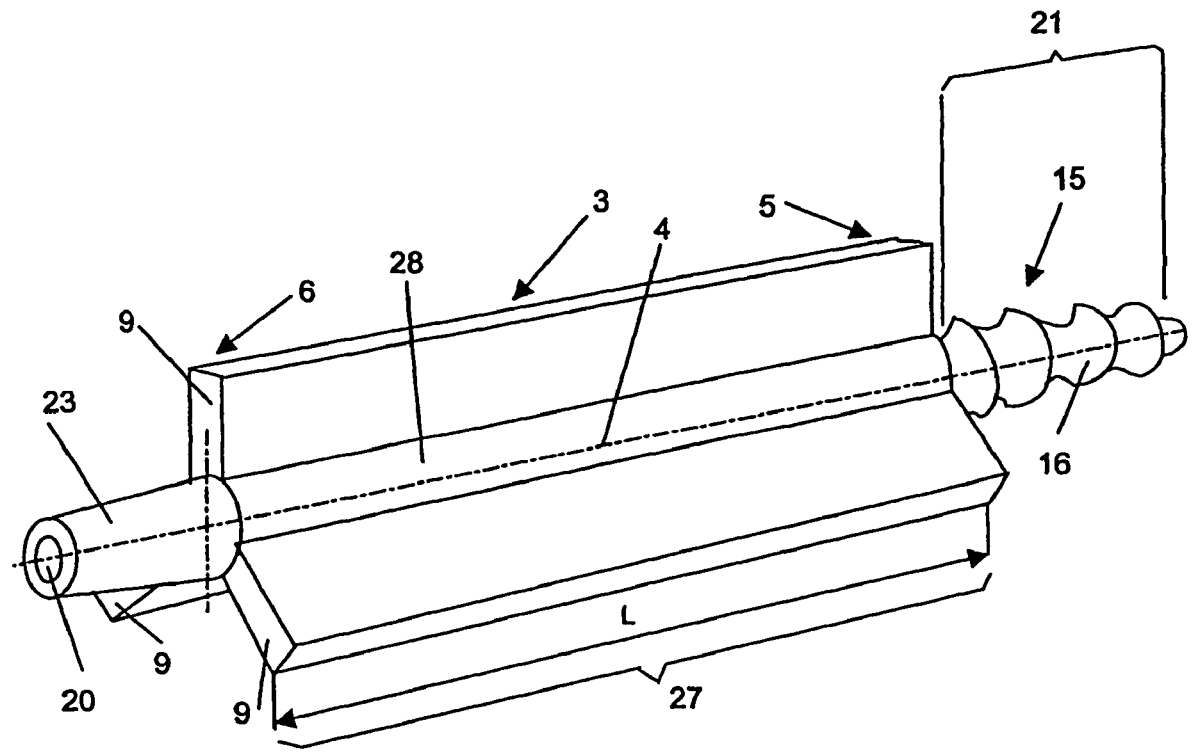
FIG. 11 is a perspective view of another embodiment of a 3-blade anchoring element that is equipped with a transport screw.

As shown in FIGS. 10 and 11, the threaded segment 21 can be integrated into the anchoring segment 27, whereby the threads protrude radially over the thickness D of the blade or protrude over the anchoring segment 27 at the front end 5 of the anchoring element 3. Moreover, the threaded segment 21 may protrude over only part of length L or over the entire length L. The advantages of this transport device 15 lie in the fact that the transport screw 16 pulls the anchoring segment 27 directly into the bone. There is the disadvantage, however, that in the middle of the spinal column the bone is very porous, so that the transport screw 16 may pull out and the transport device could fail.

Figure 12:
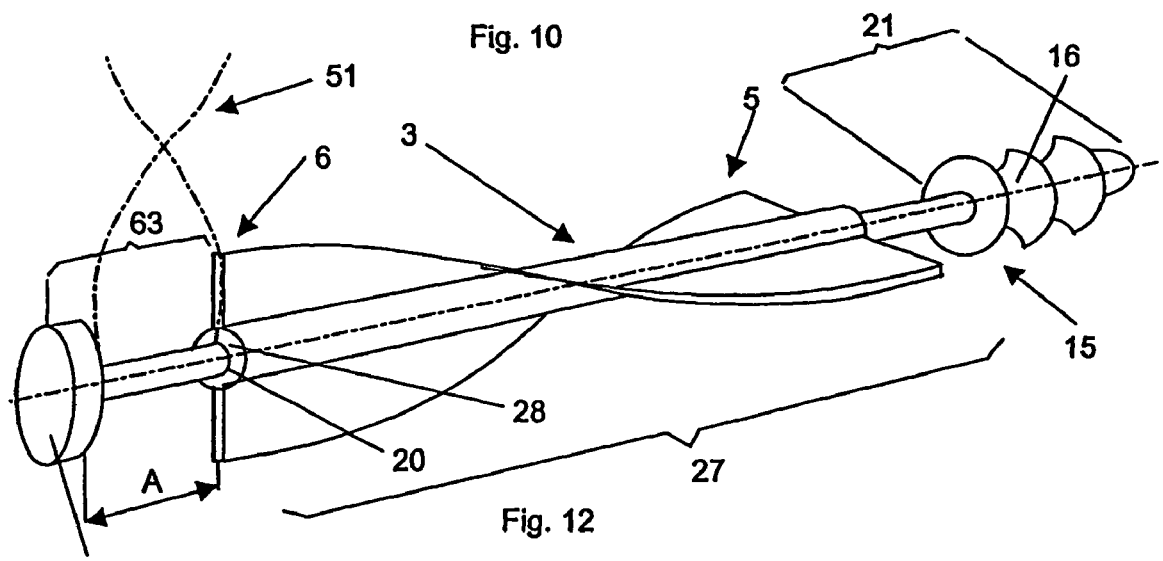
FIG. 12 is a perspective view of another embodiment of an anchoring element that is equipped with a transport device.

In FIG. 12 the transport device 15 includes a transport screw 16, which is located in the hole 20 in the hollow 28, protrudes over the front end 5 of the anchoring element 3, and can be anchored in the counter corticalis. Instead of being anchored in the counter corticalis by means of threading, as in the case of transport screw 16, other elements such as pegs 46 (FIGS. 16*a* and 16*b*) or hooks 47 (FIGS. 17*a* and 17*b*), etc., with extensions can also be used. At the back end 6 of the anchoring element 3, the transport device 15 has an extension 63 that is connected to the transport screw 16, protrudes coaxially over the anchoring element 3 over length segment A, and has an abutment 15 at the end, so that an expanding device 51 can be inserted between the abutment 50 and the back end 6 of the anchoring element 3 and the anchoring segment 27 can be forced into the bone by opening the expanding device 51. In this embodiment of the transport device 15 the transport screw 16 is anchored in the bone from the outset. The drawback, however, is the expensive instrumentation required by the limited space in which the work may be performed.

Figure 13:
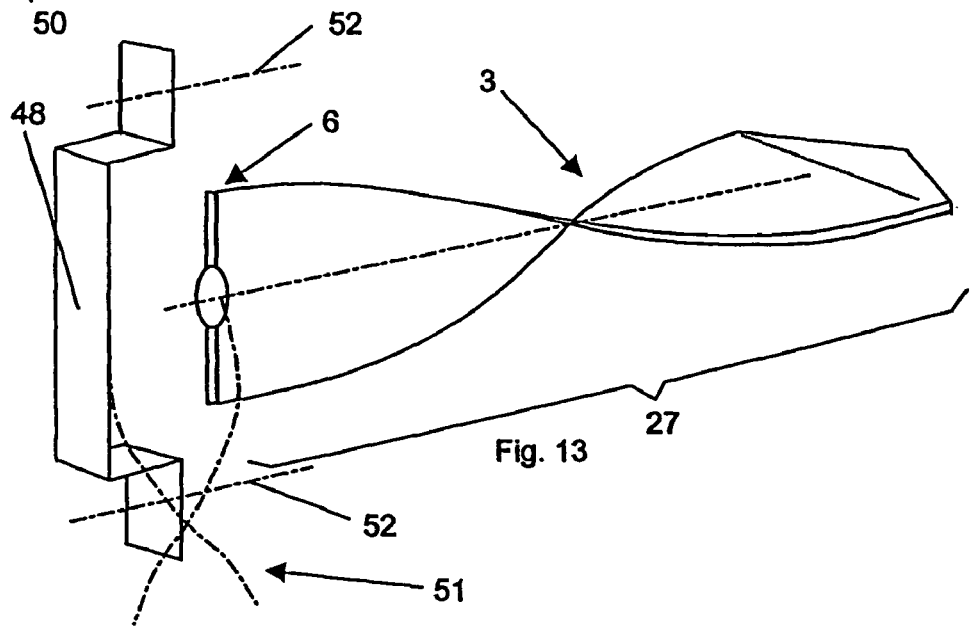
FIG. 13 is a perspective view of an implantable anchoring element with a transport device.

The U-shaped auxiliary device 48 that is symbolically depicted in FIG. 13 is anchored by means of, e.g., bone screws 52 in the cortex layer as an abutment in order to force the anchoring segment 27 at the back end 6 of the anchoring element 3 into the bone by means of an expanding device 51. Here additional drilling of the vertebral bodies may be required in order to anchor the auxiliary device 48.

Compared to bone screws as well as hollow screws, in the blade 9 the anchor strength may be relatively low in the longitudinal axis 4. The transport devices 15 shown in FIGS. 10-12 may increase the anchoring strength.

Figure 14A:
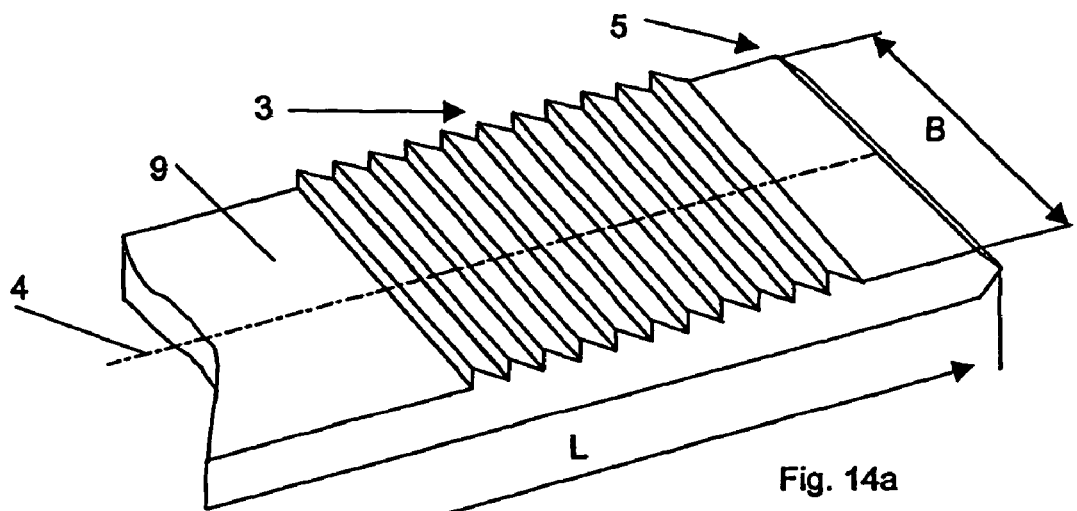
FIG. 14a is a perspective view of an embodiment of the anchoring element with a surface structure.
Figure 14B:
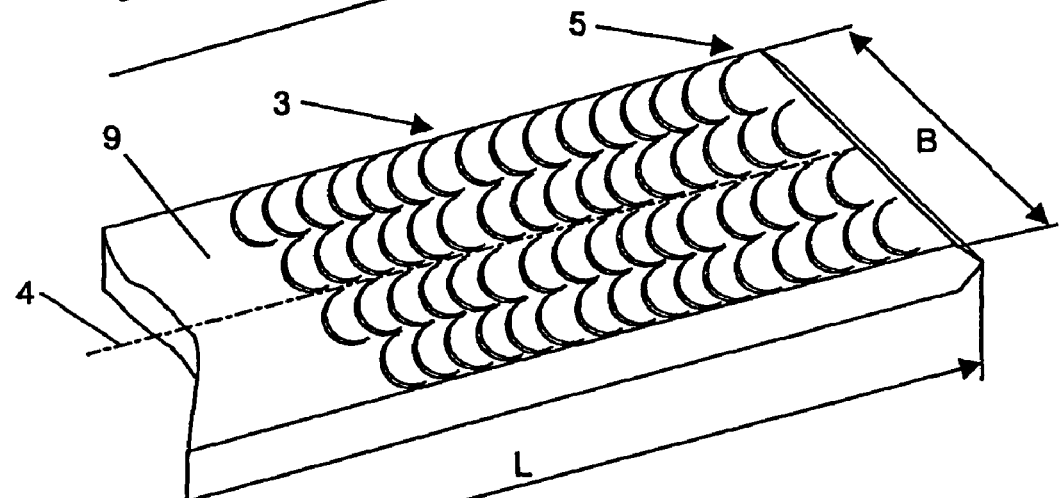
FIG. 14b is a perspective view of another embodiment of the anchoring element with a surface structure.
Figure 14C:
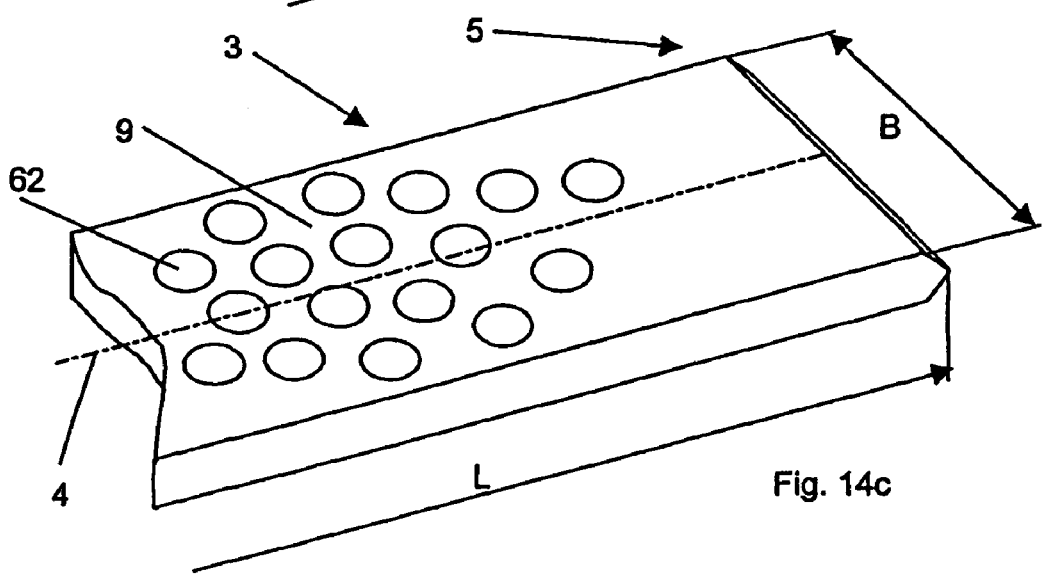
FIG. 14c is a perspective view of an embodiment of the anchoring element with transverse-running holes.

FIGS. 14*a*-14*c* show ways, without limitation, in which the design of the surface of the blade 9 may be altered to increase anchoring strength in the longitudinal axis 4:

a) A saw-toothed design of the surface of blade 9 that is enclosed by length L and width B (FIG. 14*a*), whereby the steep sides of the teeth of the saw are directed away from the front end 5 of the anchoring element 3; or 3 b) A fish-scale-like design of the surface of blade 9 that is enclosed by length L and width B (FIG. 14*b*), whereby the sides of the scales, which are steep in this case as well, are directed away from the front end 5 of the anchoring element 3.

In this case, the saw-toothed or fish-scale-like design may be applied to only one of the surfaces enclosed by length L and width B, or it can be applied to both of these surfaces; or it can encompass only a portion of length L, or it can extend over the entire length L.

c) Instead of a mechanical lock, it is also possible to use a biological lock. As FIG. 14*c* shows, in this case multiple holes 62 run through the blade 9 vertically with respect to the surfaces enclosed by length L and width B, so that the bone can grow through the holes 62.

Figure 15:
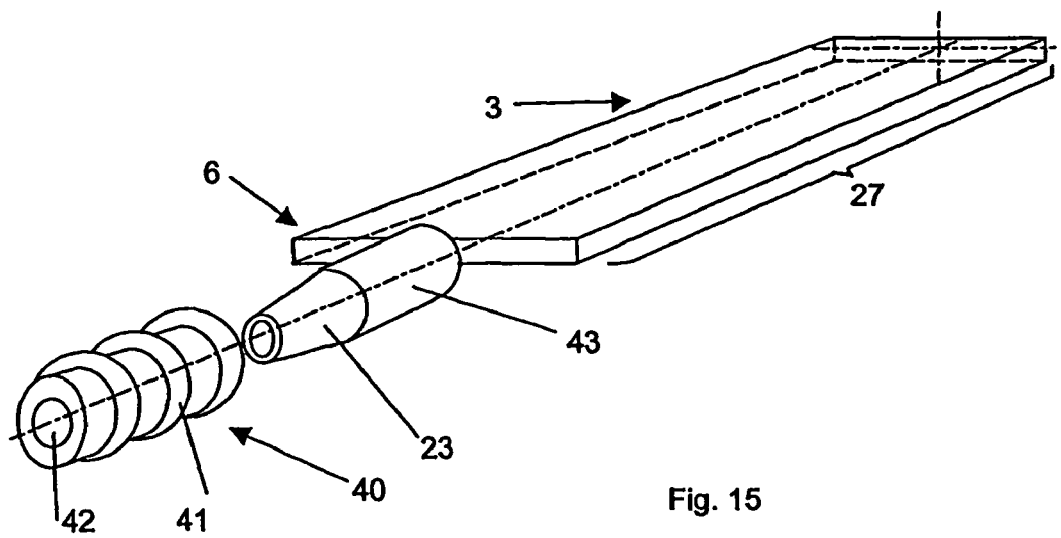
FIG. 15 is a perspective view of an embodiment of an anchoring element that is equipped with a threaded bush.

In the embodiment shown in FIG. 15, a threaded bush 40 with external threading 41 is located at the back end 6 of the anchoring element 3. The threaded bush 40 includes a coaxial hole 42, which can slide over a cylindrical pin 43 that is arranged between the anchoring segment 27 and the cone end segment 23. Like the transport screw 18 (FIGS. 10-12), this threaded bush 40 also helps to increase the anchoring strength of the anchoring element 3 in the bone. This embodiment can be used in combination with the versions shown in FIGS. 10-14.

FIGS. 16*a* and 16*b* show devices for anchoring the transport device 16 (FIG. 12) in the counter corticalis that can be used instead of a transport screw 15 (FIG. 12). This is a hollow cylindrical peg 46 that is designed to be elastically radial from its first end 56 and its second end 57 by coaxial slots 56 in the radial direction (FIG. 16*a*). In the embodiment shown in FIG. 16*a*, the radial expansion of the peg 48 is accomplished by means of two expanding cones 53 that are coaxially arranged on an also-coaxial threaded rod 54 and that can be pushed against one another by the external threading on the threaded rod and by corresponding internal threading in the expanding cones 53. As FIG. 16*b* shows, instead of the expanding cones 53 a wedge element 58 can also be used to expand the peg 46 radially. A peg 46 is shown here that has coaxially penetrating slots 55 only from the second end 57, so that the expansion of the peg 46 is accomplished by pulling the wedge element 58 inward coaxially by means of the threaded rod 54. Instead of being made of 4 parts, as shown in FIG. 16*b*, the wedge element 58 can also be composed of 1, 2, or 3 parts.

Another device for anchoring the transport device 16 (FIG. 12) in the counter corticalis is shown in FIGS. 17*a* and 17*b*. This is a hook 47 that expands radially relative to the longitudinal axis 4 of the anchoring element 3 (FIG. 1), tapers toward its tip 61, and is forced together radially both before and during installation by a coaxially arranged bush 59. The hook 47 is inserted by means of a coaxial rod 60. After the hook 47 is inserted, bush 59 is pulled off of the hook 47 over its end opposite the tip 61, whereupon the hook 47 elastically expands radially and is thus anchored in the counter corticalis.

Figure 18:
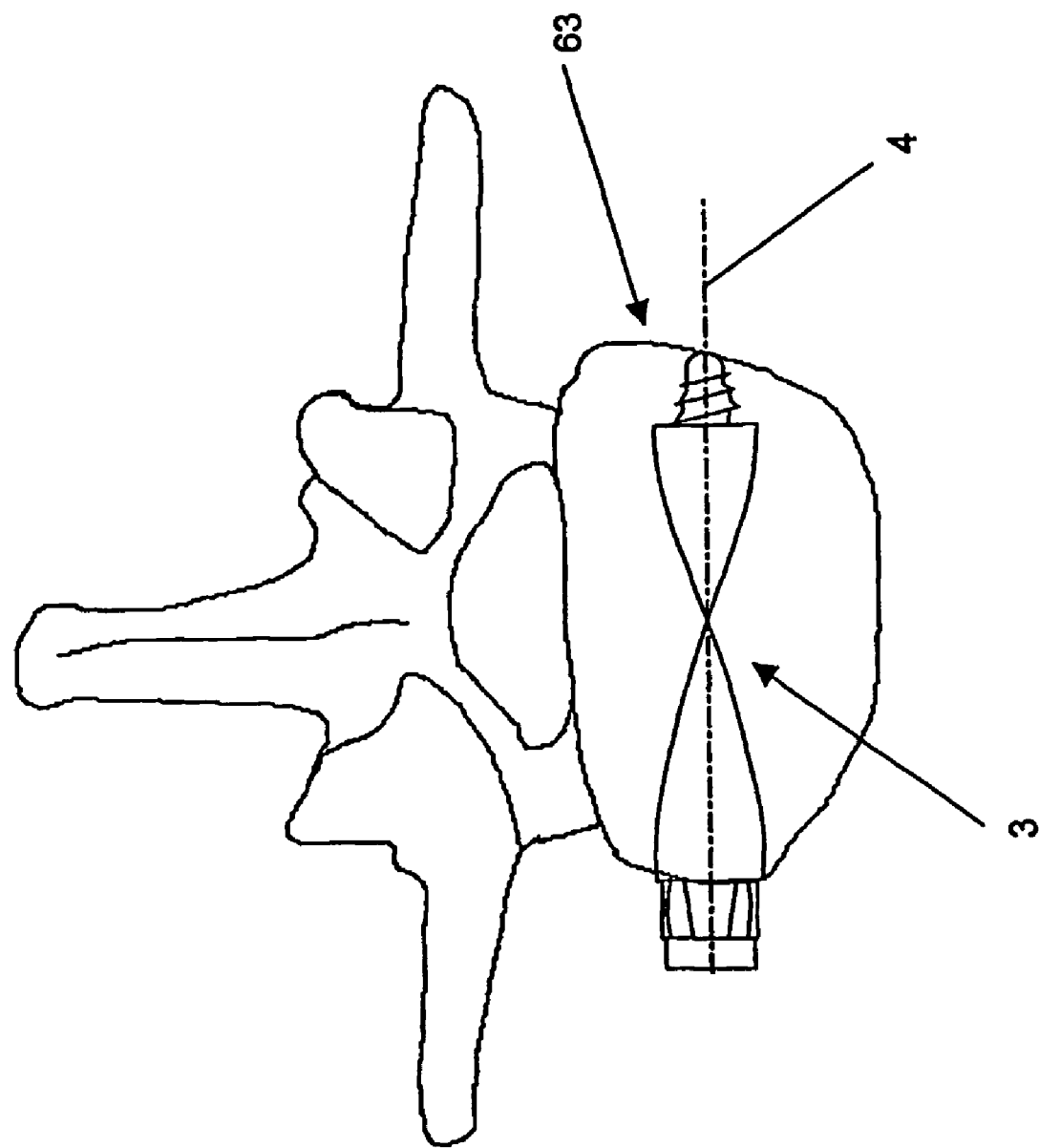
FIG. 18 is a cross-section through a vertebral body with an implanted anchoring element.

FIG. 18 shows a cross-section through a vertebral body 63 with an inserted anchoring element 3 that passes through the vertebral body 63 with a longitudinal axis 4 that runs transverse to the longitudinal axis of the spinal column.

Figure 19:
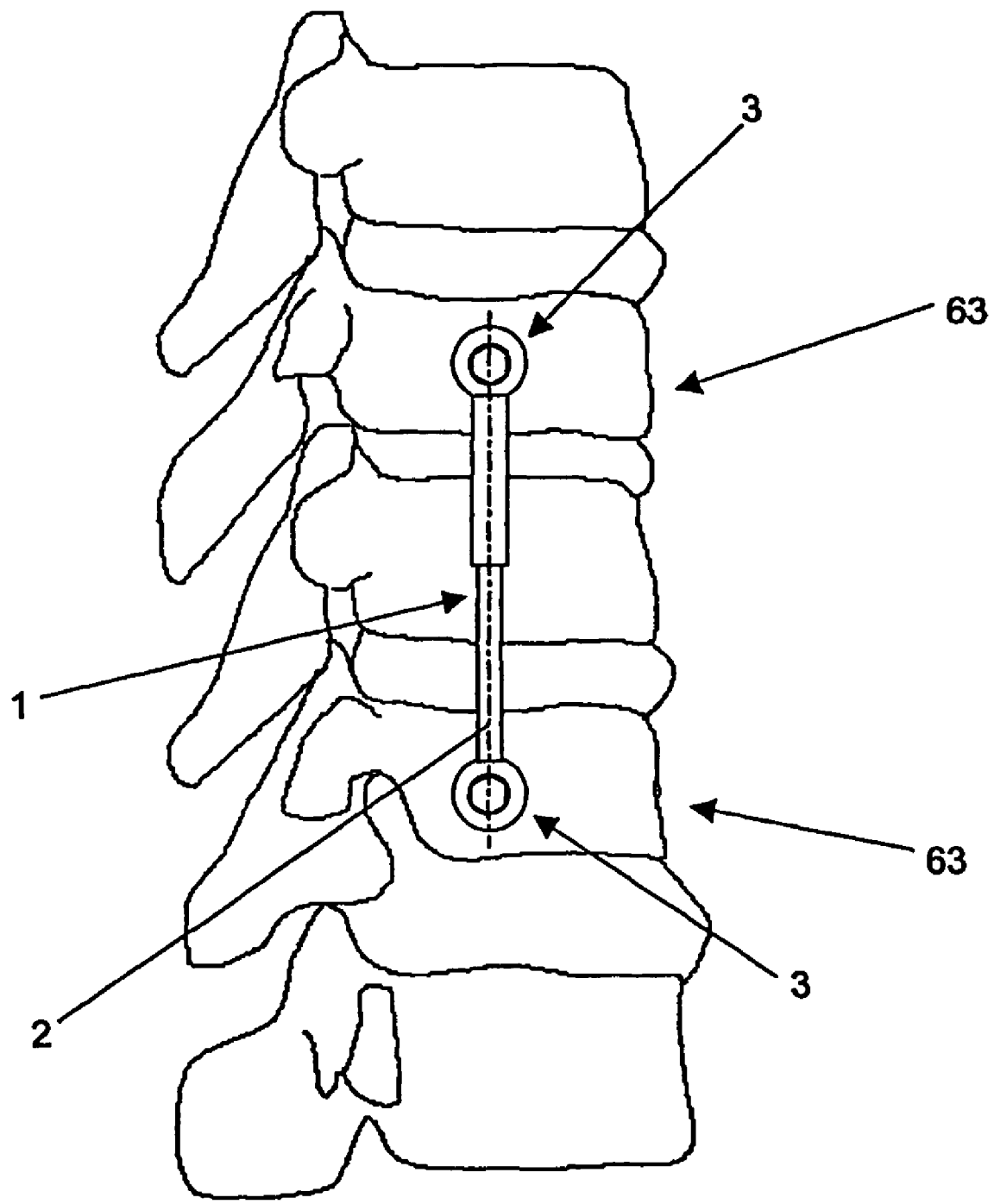
FIG. 19 is a view of a cut-out of a spinal column with an implanted device as described by the invention.

FIG. 19 shows a side view of several vertebral bodies 63 with an implanted device according to the invention which, in this embodiment, comprises a telescoping longitudinal support 1 with a central axis 2 that runs parallel to the longitudinal axis of the spinal column and two anchoring elements 3.

In use the present invention may provide a spinal-column fixation device that can be attached to the vertebral bodies by means of spiral-twisted, blade-like anchoring elements and that takes into account the following additional considerations:

a) the anchoring implants may be inserted before the longitudinal support is inserted, thus obviating the need for complicated targeting devices and for aligning the anchoring elements specifically with the longitudinal support;

b) the longitudinal support may be placed at the end of the anchoring implant;

c) connections between the longitudinal support and anchoring implant may be polyaxial, play-free, and angularly stable, and may be locked and unlocked; and d) it should be possible to insert the anchoring elements with a transport device, thereby avoiding the uncontrolled hammering.

Depending on the design of the receiving means, the angle between the longitudinal supports of the anchoring elements and the central axis of the longitudinal support may be fixed, may be varied around an axis, or may be adjusted polyaxially. The surface of the blade may also be designed in different ways on a side that is enclosed by length L and width B or on the two sides that are enclosed by length L and width B. For example, without limitation, the surface(s) of the blade may comprise:

a) a smooth surface;

b) saw-toothed;

c) fish-scale-like;

d) arrow-like teeth;

e) rough surface (for example, etched, plasma-coated, radiated); or f) holes (biological locking by virtue of the bone growing through the holes).

In this regard the surface structures may be applied on one side, on both sides, or only partially on the surface of the blade. The different blade designs can be combined with the different surfaces.

The anchoring element may be hammered in, or inserted into a vertebral body with the aid of a transport device. Uncontrolled hammering on the spinal column is generally not recommended (there is the risk of damaging neurologic and vascular structures). Suitable transport systems include, without limitation, the following:

a) a transport screw is integrated into the blade (at the tip);

b) an element (screw, pin, hook, etc. with extension) anchored in the counter-corticalis serves as an abutment so that the blade can be pulled into the bone; or c) a device is anchored in the corticalis in order to force the anchoring element into the bone.

Compared to the devices that are anchored to the vertebrae by means of screws, the invention may provide the following properties:

1) Resistance to cutting through the bone may be increased, while at the same time the amount of bone displaced may be reduced:

Same load-bearing surface area per unit of length:

Implant with 2 bone screws per vertebra with a minor diameter of d=5 mm;

Load-bearing surface area per unit of surface area: 2×d× length/length=10 mm2/mm Displacement per unit of length: 2×d2×Pi/4×length/length=39 mm2/mm Implant with blade-shaped anchoring element per vertebra with width B=10 mm, core in the middle with a diameter of d=5 mm, and a blade thickness of D=1.2 mm:

Load-bearing surface area per unit of surface area: 2×d×length/length=10 mm2/mm

Displacement per unit of length: ((B−d)×H+d2×Pi/4×length/length=25.6 mm2/mm

This shows that there is thus a reduction in displacement (excluding the threading) of 34% with the same load-bearing surface area.

Same displacement per unit of length (excluding threading):

Implant with 2 bone screws per vertebra with a minor diameter of d=5 mm;

Displacement per unit of length: 2×d2×Pi/4×length/length=39 mm2/mm

Load-bearing surface area per unit of length: 2×d×length/length=10 mm2/mm

Implant with blade-shaped anchoring element per vertebra with width B=7 mm, core in the middle with a diameter of d=5 mm, and a blade thickness of D=1.2 mm:

Displacement per unit of length: ((B−d)×H+d2×Pi/4×length/length=39 mm2/mm

Load-bearing surface area per unit of length: ((39 mm2−d2×Pi/4/H+d)×length/length=21 mm2/mm.

This shows that the load-bearing surface area is increased by 110% while displacement remains the same.

2. Devices that are anchored in the vertebral bodies with screws require at least 2 bone screws per vertebra or one bone screw combined with a clasp-like base in order to provide the rotational stability required for fusion. A blade-shaped anchoring element may be anchored in the bone in a rotationally stable manner, therefore providing the rotational stability required for successful fusion of the vertebral bodies being bridged, and thus offers the following advantages:

Devices that are connected to the spinal column cranially and caudally by one blade-shaped anchoring element apiece may be inserted higher up the spinal column than the bulky screw-anchored implants;

The fact that the number of anchoring elements required per vertebra may be reduced to one may make it faster and simpler to insert implants based on blade-shaped anchoring elements.

In one embodiment, the device for fixation of bones may comprise:

1. A) a longitudinal support (1) with a central axis (2); and B) n anchoring elements (3.i) (2≦i≦n) with the longitudinal axes (4), one front end each (5) and one back end each (6), whereby C) the longitudinal axes (4) of the anchoring elements (3.i) are arranged at an angle of between 65° and 115° relative to the central axis (2) of the longitudinal support (1); and D) at least one of the anchoring elements (3.j) (1≦j≦n) is designed in the shape of a blade, characterized by the fact that: E) at the back end (6) at least the anchoring element (3.j) comprises receiving means (7) for the longitudinal support (1) with stopping means (8; 34) for reversibly securing the connection between the longitudinal support (1) and anchoring element (3.j), and the secured connection does not permit any relative movement between the longitudinal support (1) and anchoring element (3.j), as well as taking up forces and moments in all three axial directions of a three-dimensional coordinate system.

2. The device according to 1, wherein at least the one anchoring element (3.j) (1≦j≦n) is designed in the shape of a blade abutting the back end (6) of the anchoring element (3.j).

3. The device according to 1 or 2, wherein the stopping means (8) can be operated from the back end (6) of at least the one anchoring element (3.j).

4. The device according to one of 1-3, wherein the receiving means (7) is open at the side so that the longitudinal support (1) can be inserted into the receiving means (7) transverse to the longitudinal axis (4).

5. The device according to one of 1-3, wherein the receiving means (7) is open from the back end (6) so that the longitudinal support (1) can be inserted into the receiving means (7) parallel to the longitudinal axis (4).

6. The device according to one of 1-5, wherein at least one anchoring element (3.j) comprises a transport device (15) for inserting the anchoring element (3.j) into a bone parallel to the longitudinal axis (4).

7. The device according to 6, wherein the transport device (15) is designed as a transport screw (16).

8. The device according to 7, wherein the transport screw (16) comprises a screw tip (17), a screw shaft (18), a threaded segment (21) that abuts the screw tip (17), and drive means (19), and the drive means (19) can be operated from the back end (6) of the anchoring element (3.j).

9. The device according to 8, wherein at least one anchoring element (3.j) has a through hole (20) coaxially and the transport screw (16) can be accommodated in this hole (20) in such a way that the screw tip (17) and threaded segment (21) protrude axially over the front end (5) of the anchoring element (3.j).

10. The device according to 8, wherein at least one anchoring element (3.j) has a through hole (20) coaxially and the transport screw (16) can be accommodated in this hole (20), whereby the threaded segment (21) is integrated into the anchoring element (3.j) and over a part of its circumference protrudes radially over the anchoring element (3.j) vertical to the longitudinal axis (4).

10. The device according to 8, wherein at least one anchoring element (3.j) has a through hole (20) coaxially and the transport screw (16) can be accommodated in this hole (20), whereby the threaded segment (21) is integrated into the anchoring element (3.j) and over a part of its circumference protrudes radially over the anchoring element (3.j) vertical to the longitudinal axis (4).

11. The device according to one of 1-10, wherein the back end (6) of at least one of the anchoring elements (3.j) has a coaxial cone segment (23).

12. The device according to 11, wherein the cone segment (23) has a concentric threaded hole (24) that is open at the end axially.

13. The device according to 11, wherein a concentric pin (25) with external threading axially abuts the cone segment (23) at the end.

14. The device according to one of 1-10, wherein the receiving means (7) comprise a coaxial ball head (26) that abuts the back end (6) of the anchoring element (3.j) at the end.

15. The device according to one of 1-14, wherein the anchoring element (3.j) has an anchoring segment (27) that has at least one blade (9) and abuts the back end (6) over a length (L), whereby said blade has an essentially rectangular cross-section with a thickness (D) and a width (B) and the blade (9) has a first transverse axis (22) parallel to the long sides of the cross-section.

16. The device according to one of 1-14, wherein the anchoring element (3.j) has an anchoring segment (27) that has at least one blade (9) and abuts the back end (6) over a length (L), whereby said blade, when viewed from above, converges toward the front end (5).

17. The device according to one of 1-14, wherein the anchoring element (3.j) has an anchoring segment (27) that has at least one blade (9) and abuts the back end (6) over a length (L), whereby said blade, when viewed from above, diverges toward the front end (5).

18. The device according to one of 1-14, wherein the anchoring element (3.j) has an anchoring segment (27) that has at least one blade (9) and abuts the back end (6) over a length (L), whereby said blade, when viewed from above, converges to a point (14) at the front end (5).

19. The device according to one of 1-14, wherein the anchoring element (3.j) has an anchoring segment (27) that has at least one blade (9) and abuts the back end (6) over a length (L), whereby said blade, when viewed from above, slopes down downward on one side at the front end (5).

20. The device according to one of 1-14, wherein the anchoring element (3.j) has an anchoring segment (27) that has at least one blade (9) and abuts the back end (6) over a length (L), whereby said blade, when viewed from above, is convex at the front end (5).

21. The device according to one of 1-20, wherein the anchoring element (3.j) has an anchoring segment (27) that has at least one blade (9) and abuts the back end (6) over a length (L), whereby said blade, when viewed in longitudinal section, converges to a tip at the front end (5).

22. The device according to one of 1-20, wherein the anchoring element (3.j) has an anchoring segment (27) that has at least one blade (9) and abuts the back end (6) over a length (L), whereby said blade, when viewed in longitudinal section, is attached at the front end (5) on one side.

23. The device according to one of 1-22, wherein the anchoring element (3.j) has an anchoring segment (27) that has at least one blade (9) and abuts the back end (6) over a length (L), whereby said blade, when viewed in cross-section, narrows to a point on at least one lateral surface (32).

24. The device according to one of 1-22, wherein the anchoring element (3.j) has an anchoring segment (27) that has at least one blade (9) and abuts the back end (6) over a length (L), whereby said blade, when viewed in cross-section, is attached on one side on at least one lateral surface (32).

25. The device according to one of 1-24, wherein the anchoring element (3.j) has an anchoring segment (27) that has at least one blade (9) and abuts the back end (6) over a length (L), whereby said blade is twisted over length (L) around an edge that abuts one lateral surface (32).

26. The device according to one of 1-24, wherein the anchoring element (3.j) has an anchoring segment (27) that has at least one blade (9) and abuts the back end (6) over a length (L), whereby said blade is twisted over length (L) around the longitudinal axis (4).

27. The device according to one of 1-26, wherein the anchoring element (3.j) has an anchoring segment (27) that has two blades (9) and abuts the back end (6) over a length (L).

28. The device according to 27, wherein, when viewed in cross-section, the blades (9) lie in one plane.

29. The device according to 27 or 28, wherein, parallel to the longitudinal axis (4), the blades (9) are separated by a rod.

30. The device according to 29, wherein the rod is a hollow (28) that is drilled parallel to the longitudinal axis (4).

31. The device according to one of 1-26, wherein the anchoring element (3.j) has an anchoring segment (27) that has three or more blades (9) and abuts the back end (6) over a length (L) and the anchoring segment (27) has a star-shaped cross-section.

32. The device according to one of 1-26, wherein the anchoring element (3.j) has an anchoring segment (27) has three or more blades (9) and abuts the back end (6) over a length (L), whereby the blades (9), viewed in the cross-section of the anchoring segment (27), are arranged with unequal central angles.

33. The device according to one of 1-32, wherein the anchoring element (3.j) has a coaxial hollow (28) with a hole (20) that is also coaxial and penetrates the anchoring element (3.j) from the front end (5) to the back end (6).

34. The device according to one of 1-26, wherein the anchoring element (3.j) has an anchoring segment (27) that has at least one blade (9) and abuts the back end (6) over a length (L) and at least the one blade (9) has a sawtooth surface structure, whereby the steep sides of the saw-teeth are oriented toward the back end (6) of the anchoring element (3.j).

35. The device according to 34, wherein the surface structure is attached on one side.

36. The device according to 34, wherein the surface structure is attached on both sides.

37. The device according to one of 1-33, wherein the anchoring element (3.j) has an anchoring segment (27) that has at least one blade (9) and abuts the back end (6) over a length (L) and at least the one blade (9) has a fish-scale-like surface structure, whereby the steep sides of the scales are oriented toward the back end (6) of the anchoring element (3.j).

38. The device according to 37, wherein the surface structure is attached on one side.

39. The device according to 37, wherein the surface structure is attached on both sides.

40. The device according to one of 15-30 or 33-39, wherein the anchoring segment (27), when viewed in cross-section section, has two blades (9) that lie in one plane and that are separated by a hollow (28) coaxially to the longitudinal axis (4), whereby the blades (9) have a thickness (D) of between 0.8 and 2 mm and a width (B) of between 2.5 mm and 4.5 mm and the hollow cylinder (28) has a diameter (d) of between 3 and 7 mm.

41. The device according to one of 15-40, wherein the ratio of the width (B) to the thickness (D) is basically between 1 and 14.

42. The device according to 41, wherein the ratio of the width (B) to the thickness (D) is basically between 3 and 6.

43. The device according to one of 15-42, wherein at least one blade (9) is designed in the shape of a spiral.

44. The device according to 43, wherein at least one blade (9) has a lead S of between 60 and 300 mm.

45. The device according to 44, wherein at least one blade (9) has a lead S of between 100 and 240 mm.

46. The device according to one of 43-45, wherein the twisting angle α over length (L) of the blades (9) is between 0 and 360°.

47. The device according to one of 43-45, wherein the twisting angle α over length (L) of the blades (9) is between 0 and 180°.

48. The device according to one of 43-45, wherein the twisting angle α over length (L) of the blades (9) is between 0 and 45°.

49. The device according to one of 43-45, wherein the twisting angle α over length (L) of the blades (9) is between 45 and 90°.

50. The device according to one of 15-49, wherein at least one blade (9) is twisted in the shape of a spiral and the twist runs clockwise.

51. The device according to one of 15-49, wherein at least one blade (9) is twisted in the shape of a spiral and the twist runs counter-clockwise.

While various descriptions of the present invention are described above, it should be understood that the various features can be used singly or in any combination thereof. Therefore, this invention is not to be limited to only the specifically preferred embodiments depicted herein. Further, it should be understood that variations and modifications within the spirit and scope of the invention may occur to those skilled in the art to which the invention pertains. Accordingly, all expedient modifications readily attainable by one versed in the art from the disclosure set forth herein that are within the scope and spirit of the present invention are to be included as further embodiments of the present invention. The scope of the present invention is accordingly defined as set forth in the appended claims.

What is claimed is:

1. A vertebrae fixation device for anchoring to a vertebral body of a vertebra, the vertebrae fixation device comprising:
   an anchoring element including a receiving head and an anchoring segment, the receiving head including a U-shaped channel for receiving a longitudinal support, the channel having a channel axis;
   the anchoring segment polyaxially coupled to the receiving head, the anchoring segment including a cylindrical bore coaxially aligned with a longitudinal axis of the anchoring segment, the channel axis being substantially perpendicular to the longitudinal axis of the anchoring segment, the cylindrical bore extending from a back end to a front end of the anchoring segment; and
   at least one non-threaded blade attached to the anchoring segment for anchoring the fixation device into the vertebral body, the at least one blade including a length, a width and a thickness, the width being greater than the thickness.

2. The fixation device of claim 1, further comprising a cone segment abutting the back end of the anchoring segment.

3. The fixation device of claim 1, further comprising a transport screw disposed at the front end of the anchoring segment for inserting the device into the vertebral body, the screw having a shaft at least partially extending into the cylindrical bore, the transport device having a width, the width of the transport device being greater than a diameter of the bore.

4. The fixation device of claim 1, further comprising a transport screw disposed on the front end of the anchoring segment, the transport device having a width, the width of the transport device being greater than a diameter of the bore.

5. The fixation device of claim 1, wherein the at least one blade has a spiral shape.

6. The fixation device of claim 1, wherein the at least one blade is comprised of a plurality of blades disposed at an angle relative to each other.

7. A spinal anchor for insertion into a vertebra having a vertebral body with a lateral axis, the spinal anchor comprising:
   an anchoring element having a length and defining a longitudinal axis, the anchoring element including a receiving head and an anchoring segment, the anchoring segment being moveable with respect to the receiving head, the receiving head including a U-shaped channel for receiving a longitudinal support, the channel having a channel axis, the anchoring segment having a front end and a back end;
   a cylindrical bore coaxially aligned with the longitudinal axis of the anchoring segment and extending along a full length of the anchoring segment of the body, the bore having two open ends, the channel axis being substantially perpendicular to the longitudinal axis of the anchoring segment; and
   at least one longitudinally-extending non-threaded blade adapted for anchoring the anchoring element into the vertebral body, the longitudinal axis of the anchoring element being generally parallel with the lateral axis of the vertebral body, the front end of the anchoring segment being positioned proximate a counter corticalis of the vertebral body in an anchored position, the at least one longitudinally extending blade including a length, a width and a thickness, the width being greater than the thickness.

8. The anchor of claim 7, further comprising a transport device selected from the group consisting of a screw, a pin, a peg and a hook for inserting the anchor into the vertebral body, the transport device mounted to the front end of the anchoring segment.

9. The anchor of claim 8, wherein the transport device is disposed at least partially in the bore.

10. The anchor of claim 7, wherein the at least one blade is comprised of a first blade and a second blade.

11. The anchor of claim 7, wherein the at least one blade has a spiral shape.

* * * * *